(12) United States Patent
Seo et al.

(10) Patent No.: US 11,654,109 B2
(45) Date of Patent: May 23, 2023

(54) CAVITATION SEED FOR DRUG DELIVERY, AND DRUG DELIVERY METHOD USING SAME

(71) Applicant: Pacific System Co., Ltd., Incheon (KR)

(72) Inventors: Jong Woo Seo, Incheon (KR); Jong Bum Seo, Gangwon-do (KR); Gill Soo Song, Seoul (KR)

(73) Assignee: Pacific System Co., Ltd., Incheon (KR)

( * ) Notice: Subject to any disclaimer, the term of this patent is extended or adjusted under 35 U.S.C. 154(b) by 247 days.

(21) Appl. No.: 17/225,323

(22) Filed: Apr. 8, 2021

(65) Prior Publication Data
US 2021/0267889 A1  Sep. 2, 2021

Related U.S. Application Data

(62) Division of application No. 15/577,385, filed as application No. PCT/KR2016/005631 on May 27, 2016, now Pat. No. 11,000,476.

(30) Foreign Application Priority Data

May 28, 2015 (KR) ........................ 10-2015-0075044

(51) Int. Cl.
| | |
|---|---|
| *A61K 9/127* | (2006.01) |
| *A61N 7/00* | (2006.01) |
| *A61K 9/00* | (2006.01) |
| *A61M 37/00* | (2006.01) |
| *A61B 17/22* | (2006.01) |

(52) U.S. Cl.
CPC ............ *A61K 9/127* (2013.01); *A61K 9/0009* (2013.01); *A61K 9/0014* (2013.01); *A61M 37/0092* (2013.01); *A61N 7/00* (2013.01); *A61B 2017/22008* (2013.01); *A61M 2037/0007* (2013.01)

(58) Field of Classification Search
None
See application file for complete search history.

(56) References Cited

U.S. PATENT DOCUMENTS

| | | |
|---|---|---|
| 2004/0013662 A1 | 1/2004 | Porter et al. |
| 2008/0063604 A1 | 3/2008 | Claudio |

FOREIGN PATENT DOCUMENTS

| | | |
|---|---|---|
| KR | 1020120140290 | 12/2012 |
| RU | 2532983 C2 | 12/2012 |
| WO | 2000-35351 A1 | 6/2000 |

OTHER PUBLICATIONS

Seo, Minseok, et al. "Microfluidic assembly of monodisperse, nanoparticle-incorporated perfluorocarbon microbubbles for medical imaging and therapy." Langmuir 26.17 (2010): 13855-13860.
Lin et al. "Ferulic Acid Stabilizes a Solution of Vitamins C and E and Doubles is Photoprotection of Skin", J Invest Dermatol 125: 826-832, 2005.

*Primary Examiner* — Robert A Wax
*Assistant Examiner* — Randeep Singh
(74) *Attorney, Agent, or Firm* — Husch Blackwell LLP

(57) ABSTRACT

A cavitation seed for drug delivery, and a drug delivery method using the same are disclosed. The cavitation seed according to the present invention comprises: a shell which forms the outer surface thereof to maintain the outer shape thereof within a fluid; and a core which is located inside the shell to determine buoyancy of the cavitation seed within the fluid. The cavitation seed can improve an effect of delivering a drug into a body since cavitation is induced by ultrasound at a position close to the epidermis. In addition, the cavitation seed can be applied in the delivery of various drugs as well as skin cosmetics, such as skin tone lightening agents, depilatories, hair restorers and skin fillers, skin analgesics, local anesthetics, agents for genetic diseases such as psoriasis, and agents for treatment of skin disease such as skin cancer.

2 Claims, 16 Drawing Sheets

| NAME | TRANSITION TEMPERATURE, °C | NET CHARGE AT pH 7.4 |
|---|---|---|
| DLPC | -1 | 0 |
| DMPC | 23 | 0 |
| DPPC | 41 | 0 |
| DSPC | 55 | 0 |
| DOPC | -20 | 0 |
| DMPE | 50 | 0 |
| DPPE | 63 | 0 |
| DOPE | -16 | 0 |
| DMPA-Na | 50 | -1.3 |
| DPPA-Na | 67 | -1.3 |
| DOPA-Na | -8 | -1.3 |
| DMPG-Na | 23 | -1 |
| DPPG-Na | 41 | -1 |
| DOPG-Na | -18 | -1 |
| DMPS-Na | 35 | -1 |
| DPPS-Na | 54 | -1 |
| DOPS-Na | -11 | -1 |
| DOPE-GLUTARYL-(Na)$_2$ | ~-10 | -2 |
| TETRAMYRISTOYL CARDIOLIPIN-(Na)$_2$ | 59 | -2 |
| DSPE-mPEG-2000-Na | N/A | -1 |
| DSPE-mPEG-5000-Na | N/A | -1 |
| DSPE-MALEIMIDE PEG-2000-Na | N/A | -1 |
| DOTAP-Cl | ~-0 | +1 |

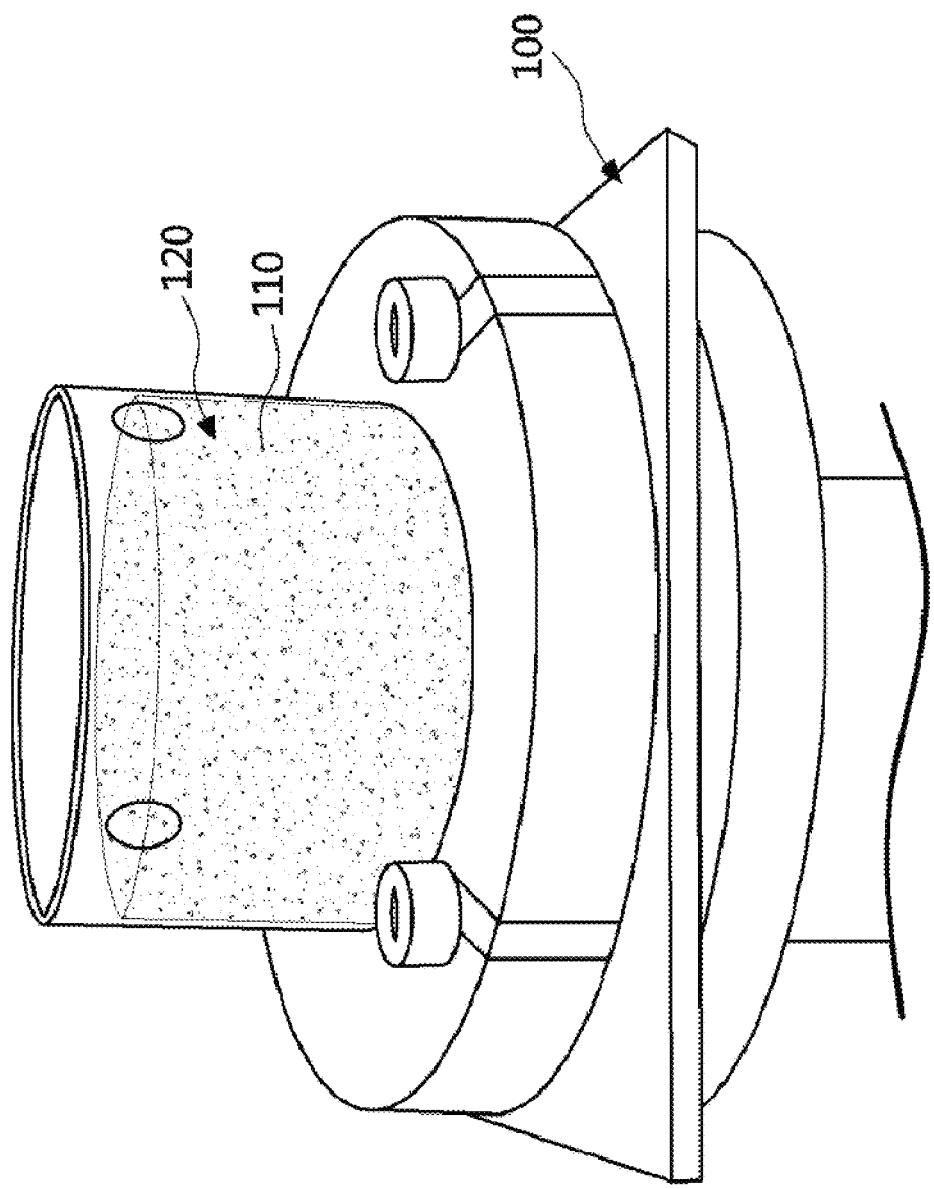

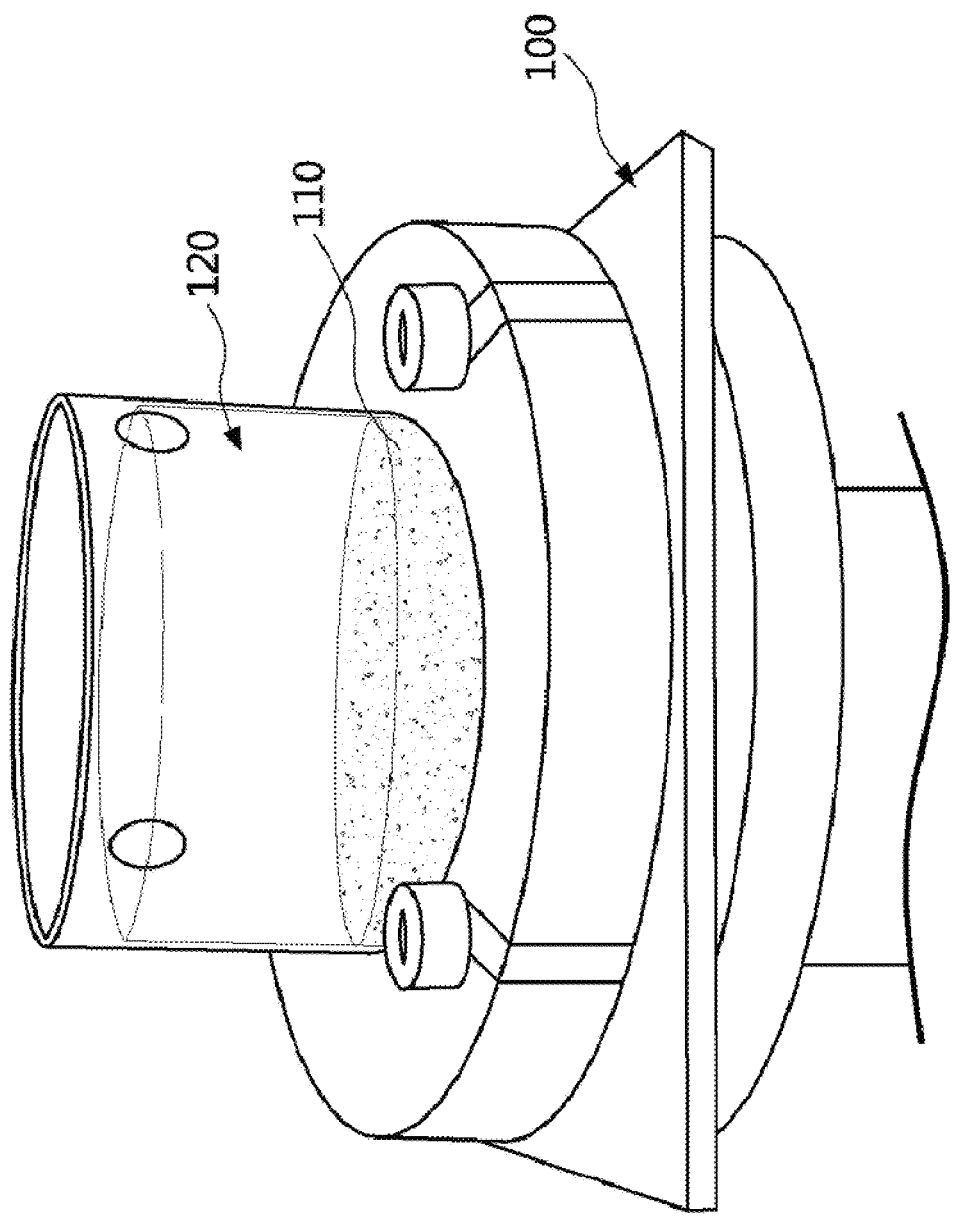

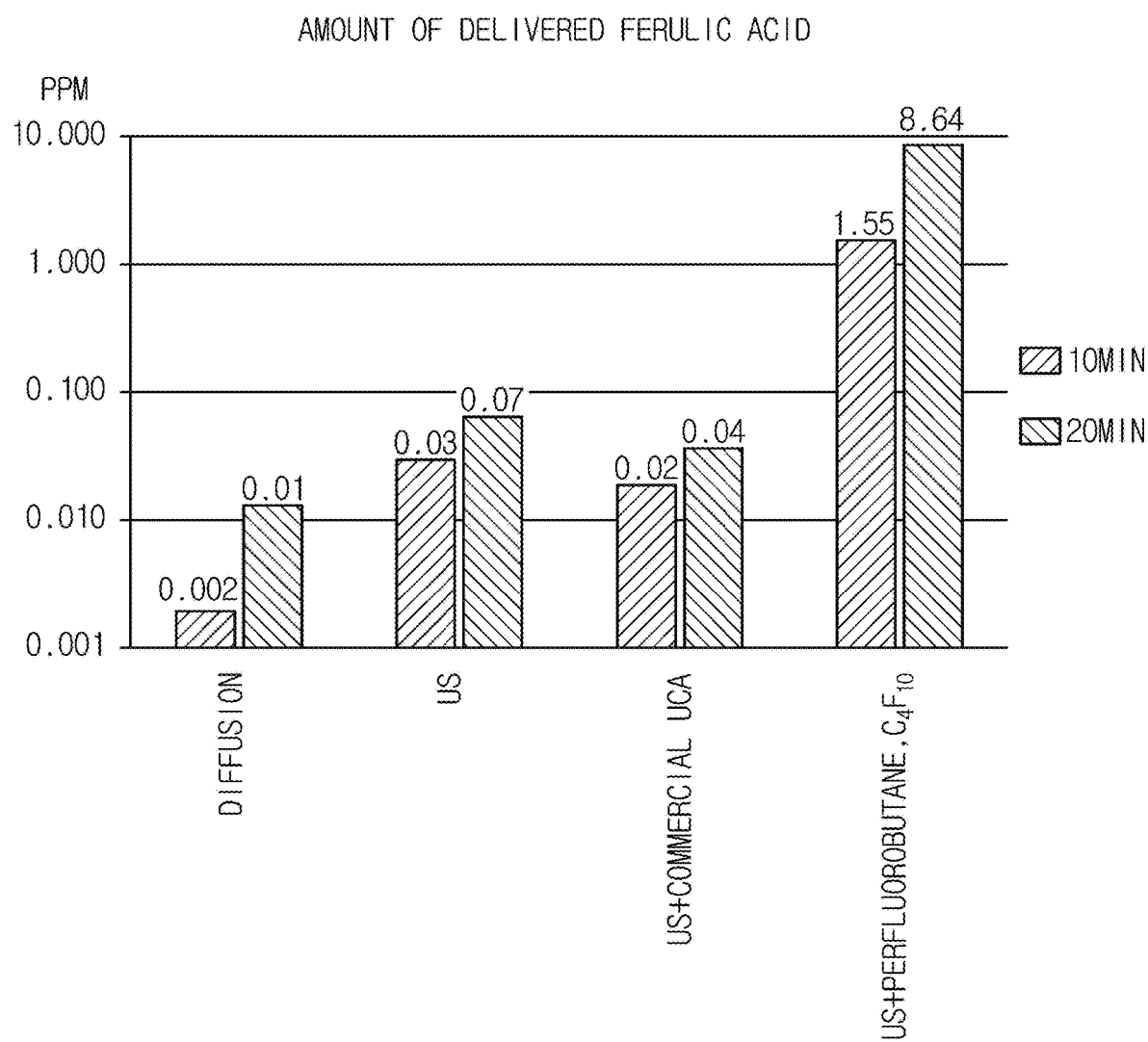

CAVITATION SEED FOR DRUG DELIVERY, AND DRUG DELIVERY METHOD USING SAME

CROSS REFERENCE TO RELATED APPLICATIONS

This application is a U.S. Divisional of U.S. Utility application Ser. No. 15/577,385, filed Nov. 28, 2017, which claims priority to International Application No. PCT/KR2016/005631 filed on May 27, 2016, which claims the benefit of priority from Korean Patent Application 10-2015-0075044 filed on May 28, 2015. The disclosures of U.S. Utility application Ser. No. 15/577,385, International Application No. PCT/KR2016/005631 and Korean Patent Application 10-2015-0075044 are incorporated herein by reference.

FIELD OF THE INVENTION

The present invention relates to a drug delivery technology, and more particularly, to cavitation seeds for delivering drugs through epidermis of human or animals and to a method using the same.

BACKGROUND OF THE INVENTION

Methods for delivering drugs may include a method using oral administration and injection, and a method using permeation through skins.

Albeit the oral administration is a representative method for delivering the drugs to a body through the mouth, it is difficult for the drugs to be delivered directly to a specific organ of the body since the drugs that have gone through a digestive system of the body may be affected.

In addition, although the injection method has a relative advantage of rapid absorption of the drugs, there is a problem that the method raises fear or pain to a person being injected, e.g., a patient.

Meanwhile, unlike the methods mentioned above, the method using permeation through skins is advantageous in that (i) the patient does not feel fear or pain during a drug delivering process, (ii) continuous drug administration is possible, and (iii) the method is relatively easy to deliver the drugs to a specific inner organ of the patient.

However, according to the existing method using permeation through skins, there is a problem since drug delivery effect is blocked by a horny layer formed on the skin.

SUMMARY OF THE INVENTION

It is an object of the present invention to solve the problems mentioned above.

It is another object of the present invention to provide cavitation seeds which can be moved to a position close to epidermis by using gravity or electric field.

It is still another object of the present invention to provide a method for delivering drugs using the cavitation seeds by inducing cavitation close to the epidermis through ultrasonic waves so as to maximize the drug delivery effect.

According to an aspect of the present invention, there is provided a cavitation seed for causing cavitation to create a cavity around the epidermis of a living body, including: a shell which forms an outer surface thereof to maintain an outer shape thereof in a fluid; and a core which is positioned inside the shell and which determines buoyancy of the cavitation seed in the fluid, wherein the cavitation seed induces cavitation by ultrasonic waves irradiated into the fluid.

Herein, the cavitation seed may induce cavitation by ultrasonic waves irradiated into the fluid.

Herein, the core may be inert liquefied gas heavier than the fluid to which the cavitation seed is added.

Herein, the inert liquefied gas may be vaporized by the ultrasonic waves.

Herein, the inert liquefied gas may be at least one selected from a group consisting of perfluoro-pentane, perfluoro-hexane, perfluoro-methylcyclo-hexane, and perfluoro-octane.

Herein, the inert liquefied gas may include perfluoro-carbon based gases or may be composed of mixtures including the perfluoro-carbon based gases.

Herein, the core may be gas that is lighter than the fluid to which the cavitation seed is added.

Herein, the gas may be perfluoro-butane.

Herein, the shell may be composed of at least one selected from a group consisting of proteins, phospholipids having hydrophilic and hydrophobic characteristics, lipoid and lipid only having hydrophobic characteristic.

Herein, the shell may have quantity of electric charges to react to the electromagnetic field.

Herein, the shell may be composed of at least one of the followings: DMPA-Na (1, 2-Dimyristoyl-sn-glycero-3-phosphate), DPPA-Na (1, 2-Dipalmitoyl-sn-glycero-3-phosphate), DOPA-Na (1, 2-Dioleoyl-sn-glycero-3-phosphate), DMPG-Na (1, 2-Dimyristoyl-sn-glycero-3-Phosphoglycerol), DPPG-Na (1, 2-Dipalmitoyl-sn-glycero-3-Phosphoglycerol), DOPG-Na (1, 2-Dioleoyl-sn-glycero-3-Phosphoglycerol), DMPS-Na (1, 2-Dimyristoyl-sn-glycero-3-phosphoserine), DPPS-Na (1, 2-Dipalmitoyl-sn-glycero-3-phosphoserine), DOPS-Na (1, 2-Dioleoyl-sn-glycero-3-phosphoserine), DOPE-Glutaryl-(Na)$_2$ (1, 2-Dioleoyl-sn-glycero-3 phosphoethanolamine), Tetramyristoyl Cardiolipin-(Na)2, DSPE-mPEG-2000-Na (1, 2-Di stearoyl-sn-glycero-3-phosphoethanolamine), DSPE-mPEG-5000-Na, D SPE-Maleimide PEG-2000-Na, and DOTAP-Cl (1, 2-dioleoyl-3-trimethylammonium propane).

Herein, the shell may include DPPC (1, 2-Dipalmitoyl-sn-glycero-3-phosphocholine) and DPPA (1, 2-Dipalmitoyl-sn-glycero-3-phosphate) at a predetermined ratio.

Herein, the fluid may be drugs delivered to the epidermis by the cavitation induced by the cavitation seed.

According to another aspect of the present invention, there is provided a method for delivering drugs to the epidermis of a living body by using cavitation seeds, including the steps of: (a) introducing to the epidermis a mixture including the cavitation seeds mixed with a fluid including the drugs; (b) adjusting electromagnetic field applied to the mixture to thereby determine positions of the cavitation seeds in the mixture; and (c) irradiating ultrasound waves onto the mixture by using an ultrasound radiator to induce cavitation of the cavitation seeds.

According to still another aspect of the present invention, there is provided a cavitation seed mixture for causing cavitation to create a cavity around the epidermis of a living body, including: a fluid; and cavitation seeds mixed with the fluid, wherein each of the cavitation seeds includes a shell which forms an outer surface thereof to maintain an outer shape thereof in the mixture and a core which is positioned within the shell to determine buoyancy of the mixture.

BRIEF DESCRIPTION OF THE DRAWINGS

The above objects and technical features of the present invention will become conspicuous from the following description of preferred embodiments given in conjunction with the accompanying drawings, wherein like reference numerals refer to like parts throughout the several views, in which:

FIG. 6 is an exemplary drawing of a table illustrating substance that may form shell of each of the cavitation seeds in accordance with one example embodiment of the present invention.

FIG. 10A is an exemplary drawing illustrating a top view of the cavitation seeds each of which has the shell with quantity of electric charges to react to electromagnetic field in accordance with one example embodiment of the present invention.

FIG. 10B is an exemplary drawing illustrating the situation in which the electromagnetic field is applied to the cavitation seeds each of which having the shell with quantity of electric charges to react to the electromagnetic field in accordance with one example embodiment of the present invention.

FIG. 11 is a graph explaining improved drug delivery effects by using the cavitation seeds each of which has the shell with quantity of electric charges to react to the electromagnetic field in accordance with one example embodiment of the present invention.

DETAILED DESCRIPTION OF THE PREFERRED EMBODIMENTS

Figure 1:
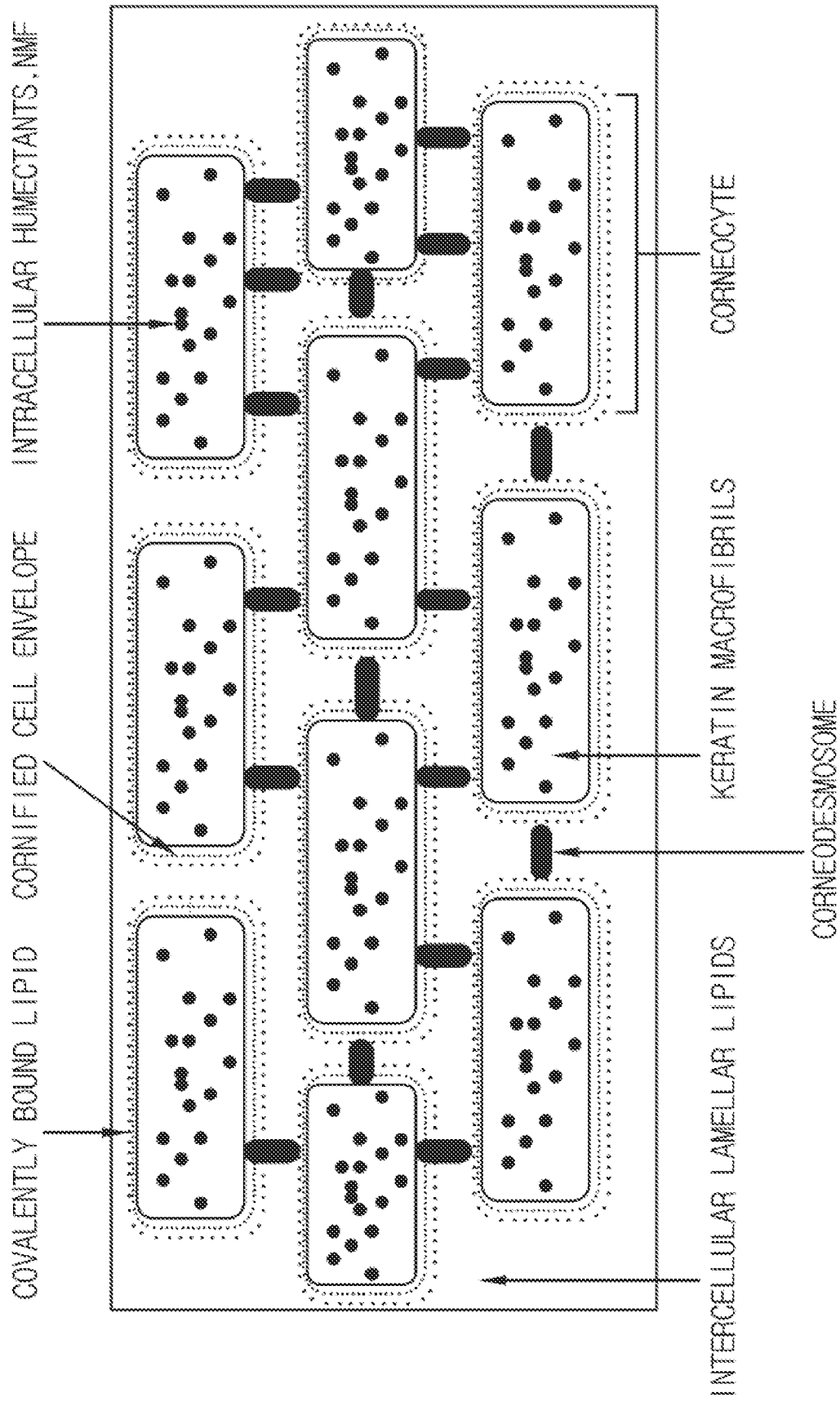
FIG. 1 is a drawing illustrating a structure of stratum corneum.

To make purposes, technical solutions, and advantages of the present invention clear, reference is made to the accompanying drawings that show, by way of illustration, more detailed example embodiments in which the invention may be practiced. These embodiments are described in sufficient detail to enable those skilled in the art to practice the invention.

It is to be appreciated that the various embodiments of the present invention, although different, are not necessarily mutually exclusive. For example, a particular feature, structure, or characteristic described herein in connection with one embodiment may be implemented within other embodiments without departing from the spirit and scope of the present invention. In addition, it is to be appreciated that the position or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

Hereinafter, preferred embodiments of the present invention will be described in detail with reference to the accompanying drawings so that those skilled in the art can easily implement the present invention.

FIG. 1 is a drawing illustrating a structure of stratum corneum. Referring to FIG. 1, the structure of the stratum corneum can be explained as "a brick and mortar model". As can be seen from this horny structure, it has a structure composed of cornified cell envelope etc., and the stratum corneum acts as important barriers to protect the human body from external substances as well as to prevent moistures from being lost.

For a reference, thickness of the stratum corneum varies depending on its position, but generally the stratum corneum has a thickness of about 100 μm. Therefore, it is difficult in delivering drugs into a body due to such a protection of the stratum corneum. There are many ways to overcome such an effect of the barriers of skins. "Sonophoresis" may be used as one among them.

Figure 2A:
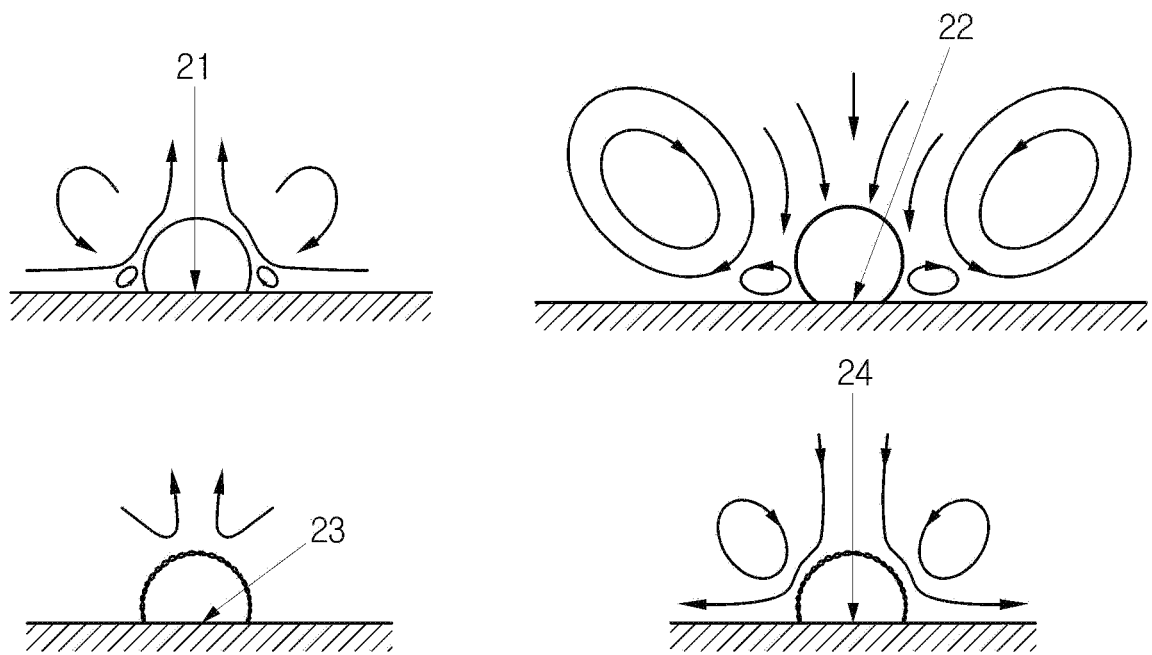
FIG. 2A is an exemplary drawing illustrating a drug delivery technology using ultrasound to deliver drugs to epidermis.
Figure 2B:
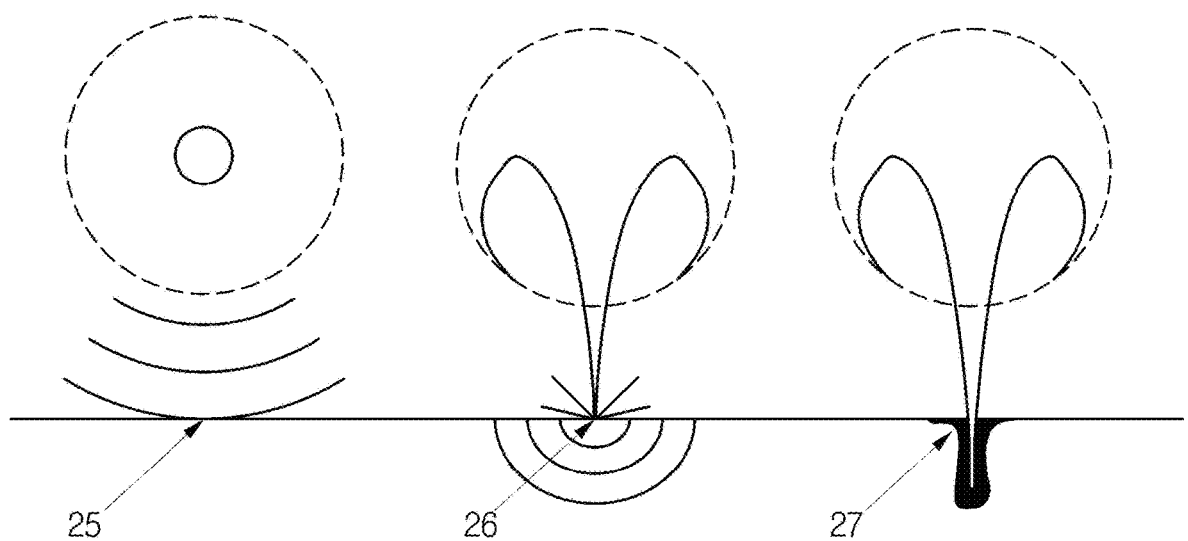
FIG. 2B is an exemplary drawing illustrating how a drug delivery channel is formed.

FIG. 2A is an exemplary drawing illustrating a drug delivery technology using ultrasound to deliver drugs to epidermis and FIG. 2B is an exemplary drawing illustrating how a drug delivery channel is formed.

Referring to FIG. 2A, a key mechanism of the Sonophoresis which uses ultrasonic waves is that bubbles generated on the epidermis or seeds capable of growing into the bubbles vibrate nonlinearly or collapse asymmetrically, by which instantly the drug delivery channel is formed. Reference numeral 21 in FIG. 2A denotes a flow of fluid generated when gas is oscillated at the skins, and reference numeral 22 denotes the fluid flow that has grown to a large extent. Reference numeral 23 designates the fluid flow that is progressive, and reference numeral 24 designates a shear stress generated around the skins due to the fluid flow. The fluid flow may cause the shear stress around the skins and as a result, it may reduce the role of the stratum corneum as the barriers.

Referring to FIG. 2B, a drug delivery process may be confirmed. Reference numeral 25 in FIG. 2B indicates the ultrasonic waves applied around the bubbles, and reference numeral 26 indicates the collapse of the bubbles in the vicinity of the epidermis by the ultrasonic waves. Reference numeral 27 designates the drug delivery channel formed according to the collapse of the bubbles in the vicinity of the epidermis. As such, if the bubbles collapse near the epidermis, strong jet streaming may occur due to asymmetric boundary conditions, thereby forming the drug delivery channel.

Ultrasound contrast agents which are composed of microbubbles may be utilized as the cavitation seeds described above. The ultrasonic contrast agents are, principally, microbubbles that make blood vessels or tissues clearly visible in ultrasound images. Such ultrasound contrast agents may be used as substance for delivering the drugs.

Figure 3:
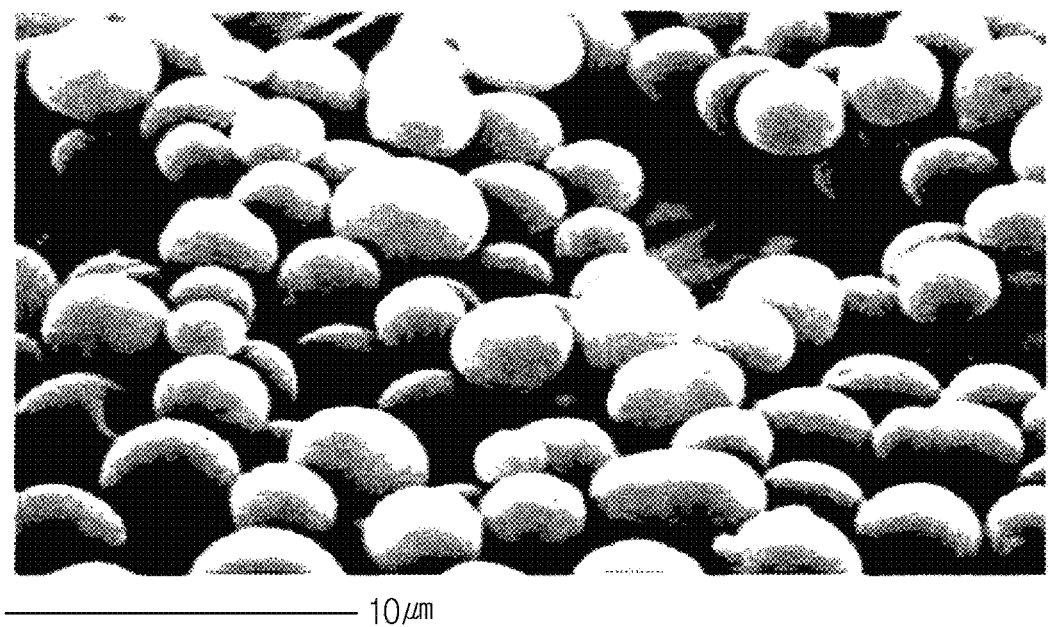
FIG. 3 is an exemplary image illustrating ultrasound contrast agents.

FIG. 3 is an exemplary image illustrating the ultrasound contrast agents.

Referring to FIG. 3, the ultrasound contrast agents are bubbles each of which has a shell containing gas therein. Herein, the shell plays the role of making the bubbles be stabilized.

In general, the ultrasound contrast agents are used for the purpose of making blood vessels and tissues more clearly visible. Thus, the ultrasound contrast agents are required to be freely flown in blood vessels. Due to this characteristic, it does not stick to the walls of the blood vessels. Further, the ultrasound contrast agents are diffused and then uniformly distributed in the flowing blood. The ultrasound contrast agents within fluid that is not flowing may have smaller size and thus buoyancy may be low, but their buoyancy may still work. Thus, they may float in upper layer depending on type of their shells.

Accordingly, the existing ultrasonic contrast agents are difficult to be located close to the epidermis including the walls of the blood vessels. Therefore, there is a limitation in delivering the drugs through the collapses of the bubbles in the vicinity of the epidermis as described above with reference to FIG. 2B.

The cavitation seeds that induce cavitation capable of creating cavity around the epidermis of a living body includes a shell that forms an outer surface of each of the cavitation seeds to maintain an outer contour of each of the cavitation seeds in the fluid into which the cavitation seeds are added, and a core which is positioned inside each shell. The core determines buoyancy of each of the cavitation seeds in the fluid. Herein, the shell and the core may be composed of materials that are biocompatible or have no materialistic side effects within the body.

The epidermis in accordance with the present invention may generally include human skin, animal skin, but it is not limited thereto, and it should be appreciated that it may include the walls of the blood vessels of a person or an animal, inner walls of viscera etc., and the like.

Herein, the cavitation seeds may induce the cavitation by the ultrasonic waves irradiated onto the fluid. Details with respect to the cavitation may refer to FIGS. 2A and 2B described above.

In addition, the fluid may be one of the drugs to be delivered to the epidermis by the cavitation induced by one of the cavitation seeds. For example, ferulic acid may be delivered to the epidermis. Certainly, necessary and various kinds of the drugs may be utilized for delivering into the body through the epidermis.

Herein, since the core serves to determine the buoyancy of each of the cavitation seeds, the buoyancy varies according to the substance of the core, and the buoyancy may determine whether or not most of the cavitation seeds are located on the epidermis.

Hence, the core for determining the buoyancy will be described in more specific detail below.

Figure 4A:
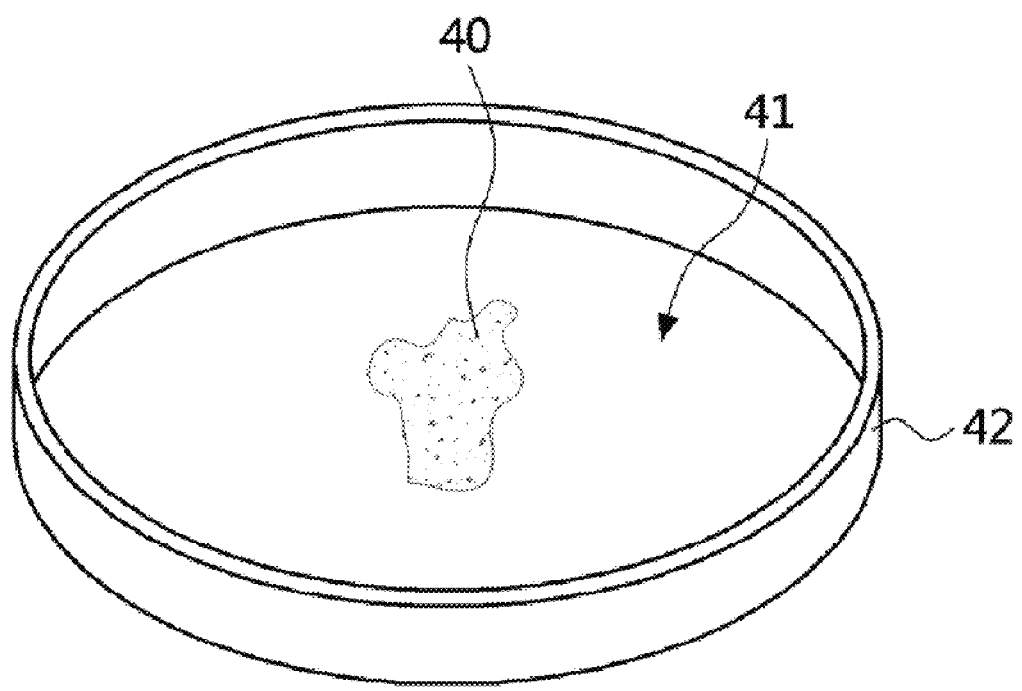
FIG. 4A is an exemplary drawing illustrating a top view of cavitation seeds whose cores include inert liquefied gas heavier than surrounding fluid in accordance with one example embodiment of the present invention.

FIG. 4A is an exemplary drawing illustrating a top view of cavitation seeds whose cores include inert liquefied gas heavier than surrounding fluid in accordance with one example embodiment of the present invention.

Figure 4B:
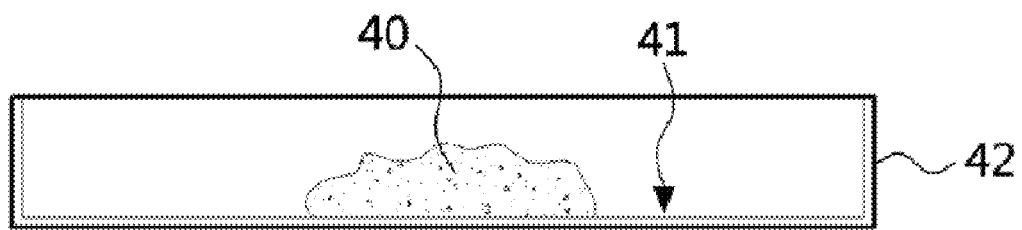
FIG. 4B is an exemplary drawing illustrating a side view of cavitation seeds whose cores include inert liquefied gas heavier than surrounding fluid in accordance with the one example embodiment of the present invention.

FIG. 4B is an exemplary drawing illustrating a side view of cavitation seeds whose cores include inert liquefied gas heavier than surrounding fluid in accordance with the one example embodiment of the present invention.

Referring to FIGS. 4A and 4B, the core may be inert liquefied gas heavier than the fluid into which the cavitation seeds are added. Such heavy cavitation seeds 40 are mixed with the fluid 41 in a schale 42 to observe changes. Herein, the fluid 41 being used is a water-based fluid, but it is not limited thereto. As shown in FIG. 4A, the cavitation seeds 40 may sink downwards in the fluid 41 due to the fact that liquefied gas heavier than the ambient fluid 41 is used. As illustrated in FIG. 4B, the side view of the cavitation seeds 40 shows that they are obviously sinked. As a result, it may be adjustable to position the cavitation seeds 40 intensively on the epidermis. Also, a size of each of the cavitation seeds 40 may be adjusted in order to place the respective cavitation seeds 40 more precisely close onto the epidermis.

Herein, the inert liquefied gas may be vaporized by the ultrasonic waves. Likewise, the cavitation may be easily induced via vaporization by the ultrasonic waves.

The inert liquefied gas may include perfluoro-carbon based gas or a mixture containing such perfluoro-carbon based gas.

For example, the inert liquefied gas may be at least one selected from a group consisting of perfluoro-pentane (whose boiling point near 30° C., density around 1.63 g/ml), perfluoro-hexane (whose boiling point near 56° C., density around 1.68 g/ml), perfluoro-methylcyclo-hexane (whose boiling point near 76° C., density around 1.788 g/ml), and perfluoro-octane (whose boiling point near 103° C., density around 1.76 g/ml). This is an preferred example and it is conspicuous for those with ordinary skill in the art to which the present invention pertains may use the inert liquefied gases of equivalent or of partially modified.

The gases set forth above are readily vaporized by the ultrasonic waves and thus the gases may be utilized as the cavitation seeds suitable for delivering the drugs.

Meanwhile, in case the fluid and the epidermis are arranged differently from the direction of the gravity, if the cavitation seeds added into the fluid are heavier than the surrounding fluid, the cavitation seeds may be further away from the epidermis. For such a case, conversely, the cavitation seeds need to be lighter than the fluid around the epidermis. Thus, for this case, the core may be a gas that is lighter than the fluid into which the cavitation seeds are added.

Figure 5A:
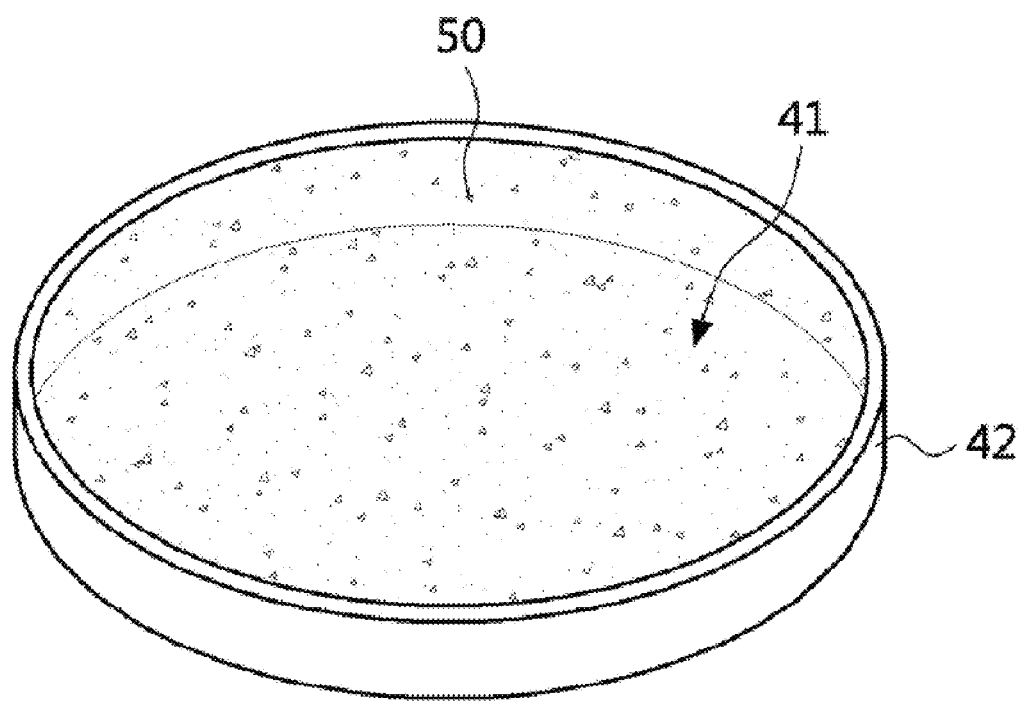
FIG. 5A is an exemplary drawing illustrating a top view of cavitation seeds whose cores include perfluoro-butane in accordance with one example embodiment of the present invention.

FIG. 5A is an exemplary drawing illustrating a top view of cavitation seeds whose cores include perfluoro-butane in accordance with one example embodiment of the present invention.

Figure 5B:
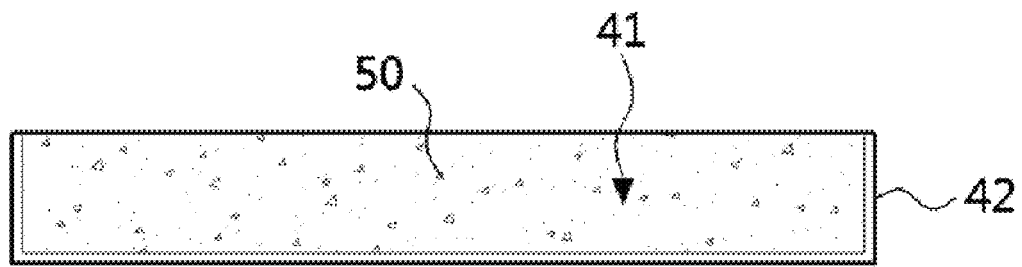
FIG. 5B is an exemplary drawing illustrating a side view of cavitation seeds whose cores include perfluoro-butane in accordance with the one example embodiment of the present invention.

FIG. 5B is an exemplary drawing illustrating a side view of cavitation seeds whose cores include perfluoro-butane in accordance with the one example embodiment of the present invention.

The perfluoro-butane is a gas that is lighter than the fluid into which the cavitation seeds are added.

Referring to FIGS. 5A and 5B, the perfluoro-butane is used as the core of each of the cavitation seeds 50 so that the cavitation seeds 50 can be lighter than the surrounding fluid 41, and the buoyancy may have a large influence thereon. The light cavitation seeds 50 are mixed with the surrounding fluid 41 in the schale 42 to observe the changes. Herein, the surrounding fluid 41 is the water-based fluid, but it is not limited thereto.

As shown in FIG. 5A, the cavitation seeds 50 are uniformly distributed in the surrounding fluid 41 as can be seen from the top view of the figure. As illustrated in FIG. 5B, the cavitation seeds 50 are uniformly distributed in the surrounding fluid 41 as can be seen from the side view of the figure as well. Therefore, the cavitation seeds 50 may be positioned close to the epidermis by offsetting the influence of the gravity. As described above, the size of each of the cavitation seeds 50 may be adjusted in order to precisely adjust a distance from the epidermis.

However, as described above, in case that the cavitation seeds are merely used for being heavier or lighter than the surrounding fluid, it may be difficult to apply the cavitation seeds to various directions since the cavitation seeds may only move in the same direction with or in the opposite direction to the gravity. For example, in case that the drugs are to be delivered to the face of a sitting person, it may be necessary to position the cavitation seeds on the epidermis with an additional force other than the gravity.

Accordingly, the shell of each of the cavitation seeds may have quantity of electric charge to react to the electromagnetic field. Hereinafter, materials which form the shell of each of the cavitation seeds and which can react to the electric field will be delineated in more detail.

FIG. 6 is an exemplary drawing of a table illustrating substance that may form the shell of each of the cavitation seeds in accordance with one example embodiments of the present invention.

With a reference to FIG. 6, the materials forming the shell of each of the cavitation seeds are described as follows.

First, the shell of each of the cavitation seeds may be at least one selected from a group consisting of proteins, phospholipids having the hydrophilic and hydrophobic characteristics, lipoid and lipids only having hydrophobic characteristic.

Phospholipids include, for example,
DLPC (1, 2-Dilauroyl-sn-glycero-3-phosphocholine),
DMPC (1, 2-Dimyristoyl-sn-glycero-3-phosphocholine),
DPPC (1, 2-Dipalmitoyl-sn-glycero-3-phosphocholine),
DSPC (1, 2-Distearoyl-sn-glycero-3-phosphocholine),
DOPC (1, 2-Dioleoyl-sn-glycero-3-phosphocholine),
DMPE (1, 2-Dimyristoyl-sn-glycero-3-phosphoethanolamine),
DPPE (1, 2-Dipalmitoyl-sn-glycero-3-phosphoethanolamine),
DOPE (1, 2-Dioleoyl-sn-glycero-3-phosphoethanolamine),
DMPA-Na (1, 2-Dimyristoyl-sn-glycero-3-phosphate),
DPPA-Na (1, 2-Dipalmitoyl-sn-glycero-3-phosphate),
DOPA-Na (1, 2-Dioleoyl-sn-glycero-3-phosphate),
DMPG-Na (1, 2-Dimyristoyl-sn-glycero-3-Phosphoglycerol),
DPPG-Na (1, 2-Dipalmitoyl-sn-glycero-3-Phosphoglycerol),
DOPG-Na (1, 2-Dioleoyl-sn-glycero-3-Phosphoglycerol),
DMPS-Na (1, 2-Dimyristoyl-sn-glycero-3-phosphoserine),
DPPS-Na (1, 2-Dipalmitoyl-sn-glycero-3-phosphoserine),
DOPS-Na (1, 2-Dioleoyl-sn-glycero-3-phosphoserine),
DOPE-Glutaryl-(Na)2(1, 2-Dioleoyl-sn-glycero-3-phosphoethanolamine),
Tetramyristoyl Cardiolipin-(Na)2,
DSPE-mPEG-2000-Na (1, 2-Distearoyl-sn-glycero-3-phosphoethanolamine),
DSPE-mPEG-5000-Na,
DSPE-Maleimide PEG-2000-Na, and
DOTAP-Cl (1, 2-Distearoyl-sn-glycero-3-phosphoethanolamine).

Referring to FIG. 6, Net Charge of various phospholipids may generally equal to zero at most of typical neutral solutions, e.g., the solutions with pH 7.4. However, it is shown in FIG. 6 that part of the materials listed in the table have the Net Charge that is not equal to zero with the solutions of pH 7.4.

Therefore, the shell may be composed of at least one of such charged phospholipids.

For example, the shell may be comprised of at least one of the followings:
DMPA-Na (1, 2-Dimyristoyl-sn-glycero-3-phosphate),
DPPA-Na (1, 2-Dipalmitoyl-sn-glycero-3-phosphate),
DOPA-Na (1, 2-Dioleoyl-sn-glycero-3-phosphate),
DMPG-Na (1, 2-Dimyristoyl-sn-glycero-3-Phosphoglycerol),
DPPG-Na (1, 2-Dipalmitoyl-sn-glycero-3-Phosphoglycerol),
DOPG-Na (1, 2-Dioleoyl-sn-glycero-3-Phosphoglycerol),
DMPS-Na (1, 2-Dimyristoyl-sn-glycero-3-phosphoserine),
DPPS-Na (1, 2-Dipalmitoyl-sn-glycero-3-phosphoserine),
DOPS-Na (1, 2-Dioleoyl-sn-glycero-3-phosphoserine),
DOPE-Glutaryl-(Na)2 (1, 2-Dioleoyl-sn-glycero-3-phosphoethanolamine),
Tetramyristoyl Cardiolipin-(Na)2,
DSPE-mPEG-2000-Na (1, 2-Di stearoyl-sn-glycero-3-phosphoethanolamine),
DSPE-mPEG-5000-Na,
DSPE-Maleimide PEG-2000-Na, and
DOTAP-Cl (1, 2-dioleoyl-3-trimethylammonium propane).

However, depending on the purpose, the cavitation seeds having the shell responsive to the electromagnetic field may be produced by using the above-described substances mixed with a certain ratio or solely by using a single substance selected among them. It is conspicuous for those skilled in the art that the substances listed above are illustrative and exemplary.

For example, the shell may be formed by combining DPPC (neutral phospholipid) and DPPA (negative polar phospholipid) at a certain ratio. More specifically, DPPC and DPPA may be diluted with the ratio of 10:1. In this case, a zetapotential of around −28 mV may be measured, and thus, the cavitation seeds having such a substance as the shells of the outer surfaces thereof may be adhered to the epidermis or vice versa, depending on the influence of the electric field.

Besides, in case that van der waals forces or magnetic fields are additionally used, pure lipids or various nanoparticle compounds may be utilized to construct the shell for each of the cavitation seeds.

Figure 7:
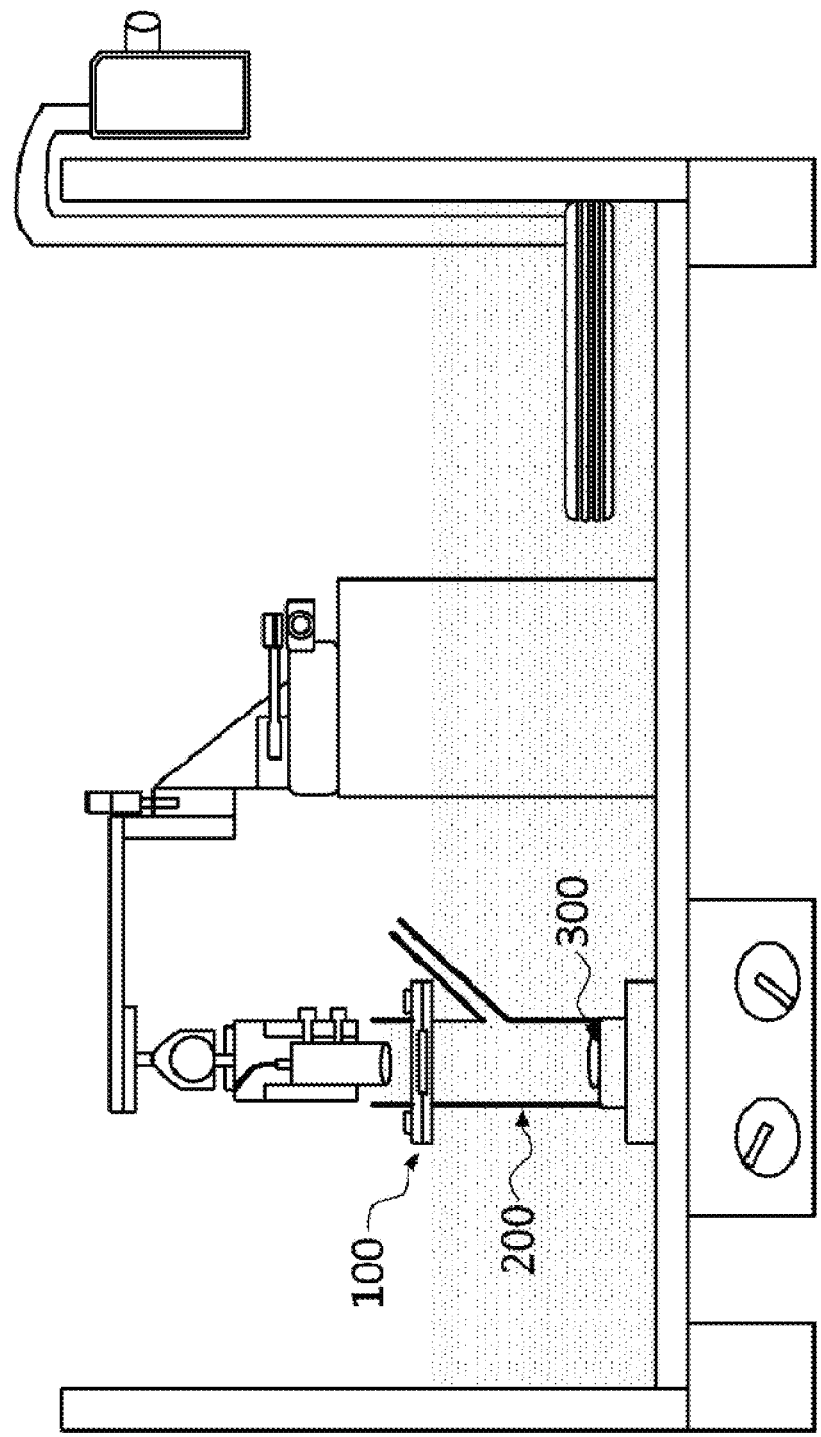
FIG. 7 is an exemplary drawing illustrating an experimental environment for confirming an effect of delivery to epidermis by using cavitation seeds in accordance with an example embodiment of the present invention.

FIG. 7 is an exemplary drawing illustrating an experimental environment for confirming an effect of delivery to epidermis by using cavitation seeds in accordance with an example embodiment of the present invention.

Referring to FIG. 7, the experimental environment may use a porcine skin 100 which is similar to a human skin, and may include a magnetic stirrer 300 used for the purpose of whipping, and a diffusion cell 200. Herein, the diffusion cell 200 indicates the upper and the lower portions of the part where the porcine skin 100 is fixed. In addition, the experimental environment illustrated in FIG. 7 should be appreciated as an example for explaining the cavitation seeds.

Herein, the porcine skin 100 is prepared by using a microtome to have a thickness of about 2 mm. For the consistency of the samples, only samples with the impedance values of both ends of the porcine skin 100 from 800 to 900 ohms are used. The porcine skin 100 is fixed to the diffusion cell 200 by a fixing device. However, it is not necessarily to be used only on such porcine skin 100, rather, it is just one example embodiment.

First, the shell of each of the cavitation seeds to be used in this experiment is formed by using DPPC which is a neutral phospholipid, and the core thereof uses perfluorohexane to generate liquefied perfluoro-hexane liposome which is heavier than the solution that is to be mixed with the cavitation seeds. For a reference, a size of each of the cavitation seeds may be adjusted to 1 μm (micro meter) or less by using a filter.

A solution containing the cavitation seeds may be prepared and produced by diluting a ferulic acid solution of 10,000 ppm to 0.100% by volume. The ferulic acid solution contains these cavitation seeds which are to be delivered to the epidermis.

Figure 8:
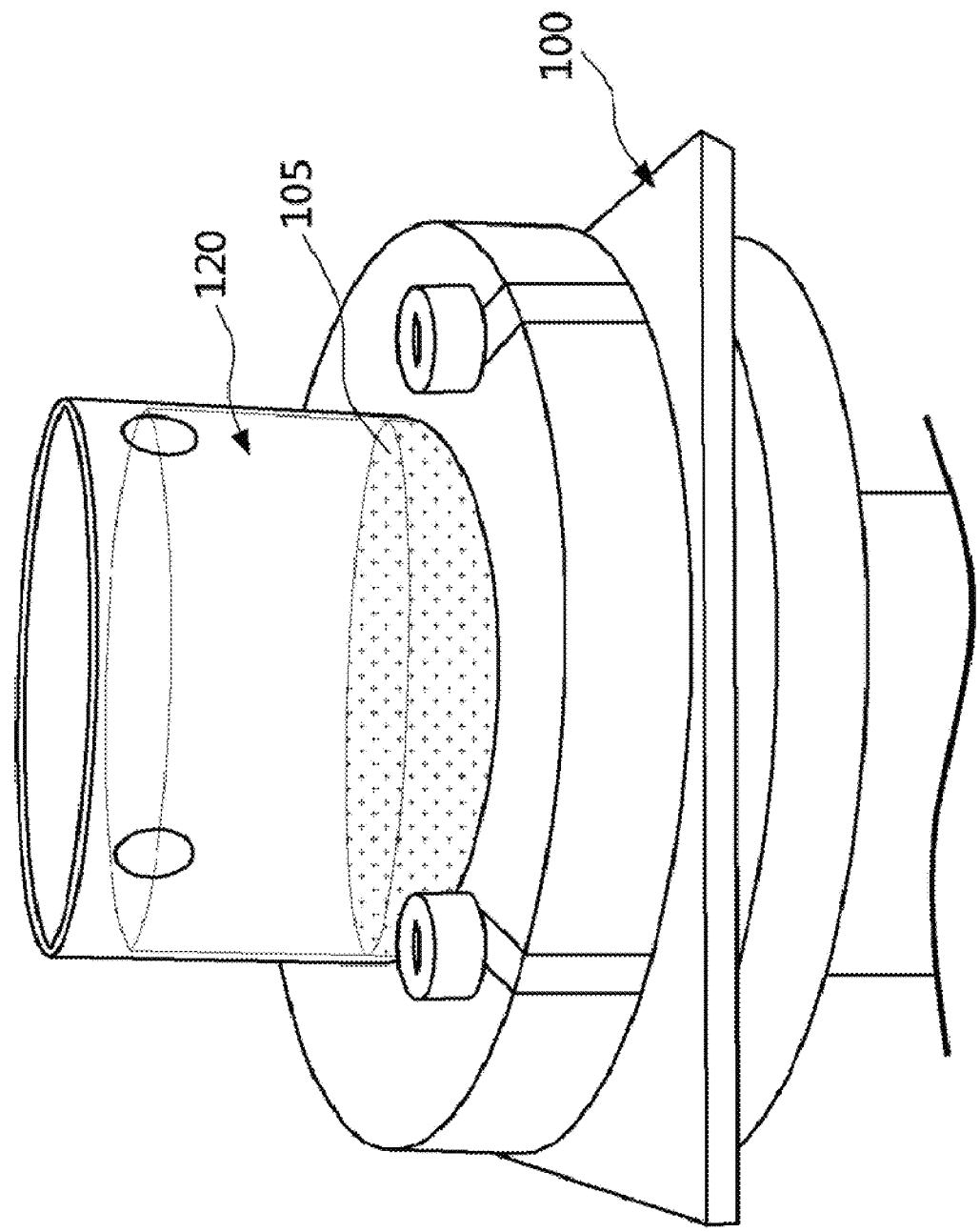
FIG. 8 is an exemplary drawing illustrating heavy cavitation seeds positioned near the epidermis in accordance with one example embodiment of the present invention.

FIG. 8 is an exemplary drawing illustrating heavy cavitation seeds positioned near the epidermis in accordance with one example embodiment of the present invention. And FIG. 9 is a graph explaining an improved effect of drug delivery in case the heavy cavitation seeds are used in accordance with one example embodiment of the present invention.

Referring to FIG. 8, under the experiment environment illustrated in FIG. 7 described above, if the ferulic acid solution 120 is put into the diffusion cell 200, due to the fact that the cavitation seeds 105 are heavier in the ferulic acid solution 120, it may be possible to intensively position the cavitation seeds 105 onto the porcine skin 100.

Roughly, ultrasonic waves of 2 W/cm² are applied to the ferulic acid solution 120 for 20 minutes. The amount of delivered ferulic acid is collected every 10 minutes, and may be quantitatively measured by High Precision Liquid Chromatography (HPLC). Herein, time and intensity of applying the ultrasonic waves may be determined via various ways by an ordinary skilled person in the art that the present invention pertains to, and it is not limited to the experimental example herein.

Figure 9:
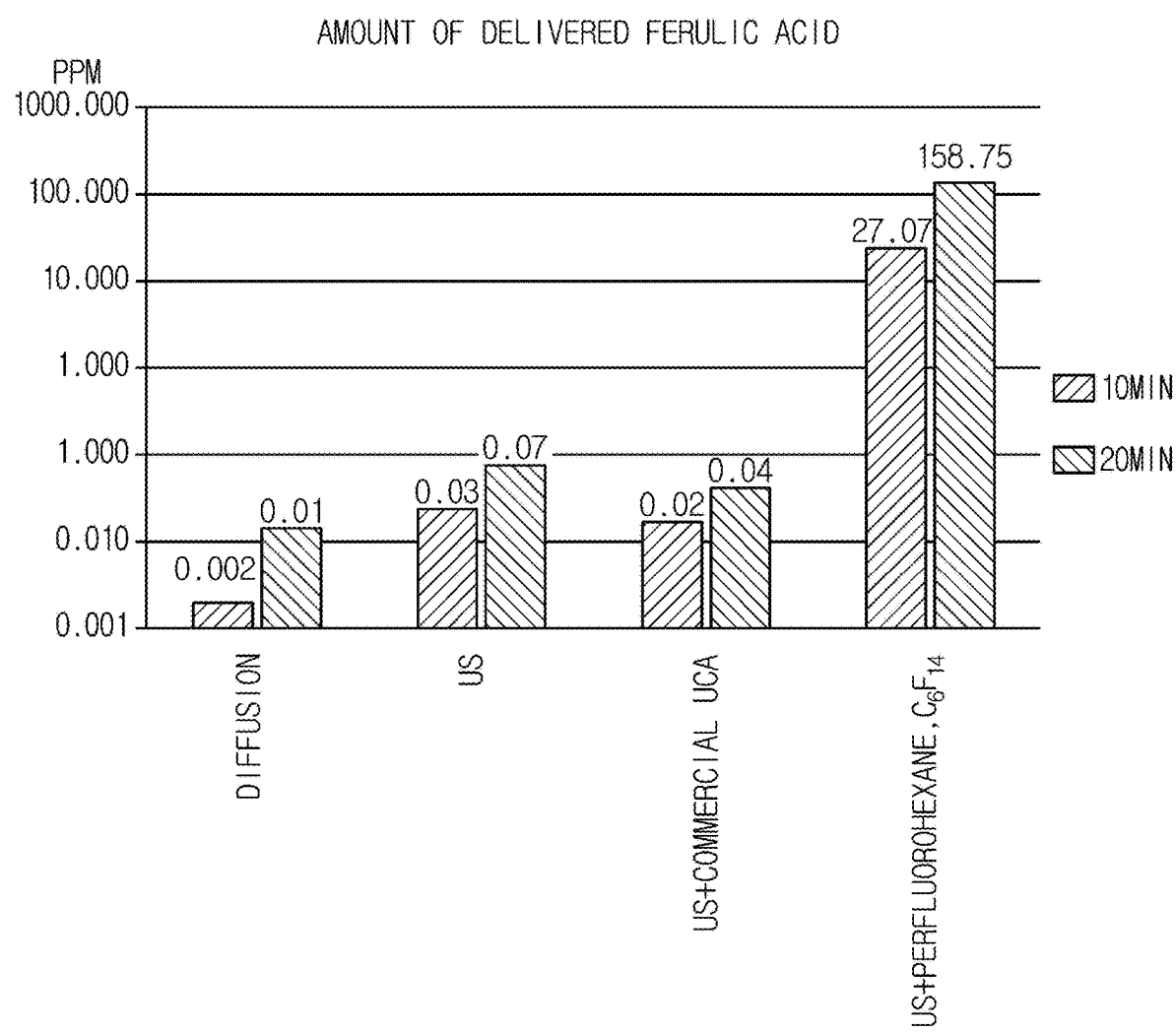
FIG. 9 is a graph explaining an improved effect of drug delivery in case the heavy cavitation seeds are used in accordance with one example embodiment of the present invention.

Referring to FIG. 9, the amounts of delivered ferulic acid according to the conventional way of irradiating the ultrasonic waves or those according to another conventional way of irradiating the ultrasonic waves with the contrast agents are improved up to 10 times higher than those of simple diffusion.

Contrarily, the amounts of delivered ferulic acid according to the present invention in which the ultrasonic waves are irradiated onto the cavitation seeds are improved up to 10,000 times as compared to results of the simple diffusion.

FIG. 10A is an exemplary drawing illustrating a top view of the cavitation seeds each of which has the shell with quantity of electric charges to react to electromagnetic field in accordance with one example embodiment of the present invention.

FIG. 10B is an exemplary drawing illustrating the situation in which the electromagnetic field is applied to the cavitation seeds each of which having the shell with quantity of electric charges to react to the electromagnetic field in accordance with one example embodiment of the present invention.

FIG. 11 is a graph explaining enhanced drug delivery effects by using the cavitation seeds each of which has the shell with quantity of electric charges to react to the electromagnetic field in accordance with one example embodiment of the present invention.

Referring to FIG. 10A, the porcine skin 100 used in the embodiments described with reference to FIGS. 8 and 9 is also used in the example embodiment described throughout FIGS. 10A to 11 as well, and the porcine skin 100 is prepared to have a thickness of about 2 mm. For the consistency of the samples, only samples with the impedance values from 800 to 900 ohms at both ends of the samples are used for tests.

Besides, preparing each shell having quantity of electric charges to react to the electromagnetic field by mixing two phospholipids, DPPC and DPPA, at a ratio of 10:1, and each core inside the shell may be filled with perfluoro-butane to form each cavitation seed 110.

The plurality of cavitation seeds 110 may be mixed with the ferulic acid solution 120 by a ratio of 0.1%.

In case that the mixed ferulic acid solution 120 is put into the diffusion cell 200, the cavitation seeds 110 are widely spread and distributed as can be seen from FIG. 10A. The reason for this may be the buoyancy acting greater than the gravity since the core of each of the cavitation seeds is filled with the perfluoro-butane.

Herein, if electrodes are put and an electric field of 15 V is applied to provide the electric field, the cavitation seeds 110 may be induced to intensively position on the porcine skin 100 as shown in FIG. 10B.

Approximately, ultrasonic waves of 2 W/cm² are applied for 20 minutes as the example embodiments describe above in the same manner, and the amount of delivered ferulic acid is collected every 10 minutes and may be quantitatively measured by High Precision Liquid Chromatography (HPLC).

Referring to FIG. 11, the amounts of delivered ferulic acid according to the way of irradiating the ultrasonic waves or those according to the way of irradiating ultrasonic waves after adding the contrast agents are improved up to 10 times as compared to those according to the simple diffusion.

However, in case of using the cavitation seeds having the shell with quantity of electric charges to be influenced by the electromagnetic field, the amounts of delivered ferulic acid may be enhanced up to about 800 times as compared to those of the simple diffusion.

In addition, results of the experiment described above may further be improved by adjusting the intensity of the electric field.

Figure 12:
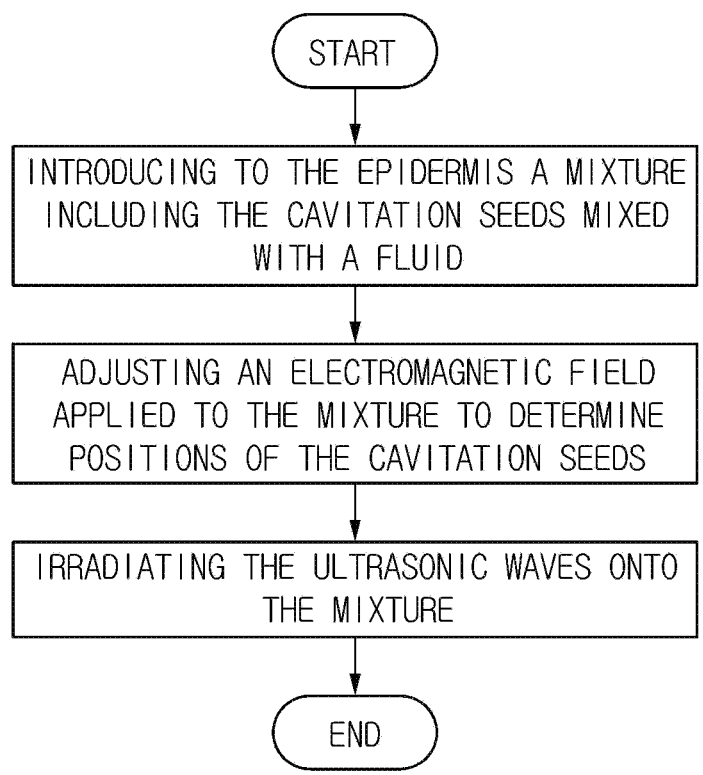
FIG. 12 is a flowchart illustrating a method for delivering drugs to the epidermis by using the cavitation seeds in accordance with one example embodiment of the present invention.

FIG. 12 is a flowchart illustrating a method for delivering drugs to the epidermis by using the cavitation seeds in accordance with one example embodiment of the present invention.

Referring to FIG. 12, a method for delivering drugs to the epidermis of a living body by using the cavitation seeds may include a step of introducing to the epidermis a mixture including the cavitation seeds mixed with a fluid including the drugs (S120), a step of adjusting the electromagnetic field applied to the mixture to thereby determine positions of the cavitation seeds in the mixture (S121), and a step of irradiating the ultrasonic waves onto the mixture by using an ultrasonic radiator to cause cavitation of the cavitation seeds (S122).

Herein, the ultrasonic radiator may be various apparatuses that are easily available to the ordinary artisan in the field pertaining to the present invention.

Herein, each of the cavitation seeds may include the core that determines the buoyancy thereof in the mixture.

Herein, each of the cavitation seeds may include the shell which forms the outer surface thereof to maintain the contour thereof in the mixture, and the shell may be charged to react to the electromagnetic field.

A cavitation seed mixture that causes cavitation to create cavity around the epidermis of a living body includes a fluid and the cavitation seeds mixed with the fluid, and each of the cavitation seeds includes the shell which forms the outer surface thereof to maintain the outer shape thereof in the mixture and the core which is positioned within the shell to determine the buoyancy of each of the cavitation seeds in the mixture.

Herein, the fluid may be an aqueous solution with which ferulic acid is diluted at a predetermined ratio.

Herein, the fluid may be at least one cosmetically or pharmaceutically acceptable drug selected from a group consisting of skin tone lightening agents, depilatories, hair restorers, skin fillers, collagens, analgesics, local anesthetics, therapeutic dielectrics, and cancer treatment agents.

Herein, the shell with quantity of electric charges may react to the electromagnetic field.

The present invention, after intensively positioning the cavitation seeds capable of inducing the cavitation at ideal positions close to the epidermis, may increase the drug delivery efficiency to the epidermis by causing the cavitation through applying appropriate ultrasonic parameters.

In addition, the present invention may be applied not only to skin treatments such as skin tone lightening agents, depilatories, hair restorers, skin fillers, skin analgesics, local anesthetics, agents for genetic diseases such as psoriasis, agents for treatment of skin disease such as skin cancer etc., but to various drug delivery methods as well.

The present invention has an effect of improving drug delivery efficiency due to the cavitation induced by the ultrasonic waves at ideal positions close to the epidermis.

Further, the present invention may have an effect of not only providing applications in skin treatments such as skin tone lightening agents, depilatories, hair restorers, skin fillers, skin analgesics, local anesthetics, agents for genetic diseases such as psoriasis, agents for treatment of skin disease such as skin cancer and the like, but also providing applications in various drug delivery.

The embodiments of the present invention as explained above can be implemented in a form of executable program command through a variety of computer means recordable to computer readable media. The computer readable media may include solely or in combination, program commands, data files, and data structures. The program commands recorded to the media may be components specially designed for the present invention or may be usable to a skilled artisan in a pertinent field. Computer readable record media include magnetic media such as hard disk, floppy disk, and magnetic tape, optical media such as CD-ROM and DVD, magneto-optical media such as floptical disk and hardware devices such as ROM, RAM, and flash memory specially designed to store and carry out programs. Program commands include not only a machine language codes made by a complier but also a high level codes that can be used by an interpreter etc., which is executed by a computing device. The aforementioned hardware device can work as more than a software module to perform the technical features of the present invention and they can do the same in the opposite case.

As seen above, the present invention has been specifically described by such matters as detailed components, limited embodiments, and drawings. While the invention has been shown and described with respect to the preferred embodiments, it, however, may be appreciated by those skilled in the art that various changes and modifications may be made without departing from the spirit and the scope of the present invention as defined in the following claims.

Accordingly, the thought of the present invention must not be confined to the explained preferred or example embodiments, and the following patent claims as well as everything including variations equal or equivalent to the patent claims pertain to the category of the thought of the present invention.

What is claimed is:

1. A method for delivering drugs to the epidermis of a living body by using cavitation seeds, comprising the steps of:
   (a) introducing to the epidermis a mixture including the cavitation seeds mixed with a fluid including the drugs;
   (b) adjusting electromagnetic field applied to the mixture to thereby determine positions of the cavitation seeds in the mixture; and
   (c) irradiating ultrasound waves onto the mixture by using an ultrasound radiator to induce cavitation of the cavitation seeds,
   wherein each of the cavitation seeds comprises:
   a shell which forms an outer surface thereof to maintain the outer shape thereof in the mixture; and
   a core which is positioned inside the shell and which determines buoyancy of the cavitation seeds in the mixture,
   wherein each of the cavitation seeds induces cavitation by the ultrasound waves irradiated onto the mixture, and
   wherein the shell comprises (I) at least one neutral phospholipid selected from a first group consisting of DLPC (1,2-Dilauroyl-sn-glycero-3-phosphocholine), DMPC (1,2-Dimyristoyl-sn-glycero-3-phosphocholine), DPPC(1,2-Dipalmitoyl-sn-glycero-3-phosphocholine), DSPC(1,2-Distearoyl-sn-glycero-3-phosphocholine), DOPC(1,2-Dioleoyl-sn-glycero-3-phosphocholine), DMPE(1,2-Dimyristoyl-sn-glycero-3-phosphoethanolamine), DPPE(1,2-Dipalmitoyl-sn-glycero-3-phosphoethanolamine), DOPE(1,2-Dioleoyl-sn-glycero phosphoethanolamine) and (II) at least one negative polar phospholipid selected from a second group consisting of DMPA-Na(1,2-Dimyristoyl-sn-glycero-3-phosphate), DPPA-Na(1,2-Dipalmitoyl-sn-glycero-3-phosphate), DOPA-Na(1,2-Dioleoyl-sn-glycero-3-phosphate), DMPG-Na(1,2-Dimyristoyl-sn-glycero-3-Phosphoglycerol), DPPG-Na(1,2-Dipalmitoyl-sn-glycero Phosphoglycerol), DOPG-Na(1,2-Dioleoyl-sn-glycero-3-Phosphoglycerol), DMPS-Na(1,2-Dimyristoyl-sn-glycero-3-phosphoserine), DPPS-Na (1,2-Dipalmitoyl-sn-glycero-3-phosphoserine), DOPS-Na(1,2-Dioleoyl-sn-glycero-3-phosphoserine), DOPE-Glutaryl-(Na)2(1,2-Dioleoyl-sn-glycero-3-phosphoethanolamine), Tetramyristoyl Cardiolipin-(Na)2, DSPE-mPEG-2000-Na(1,2-Distearoyl-sn-glycero-3-phosphoethanolamine), DSPE-mPEG-5000-Na, DSPE-Maleimide PEG-2000-Na, and DOTAP-C1 (1,2-dioleoyl-3-trimethylammonium propane).

2. The method according to claim 1, wherein the shell has quantity of electric charge for reacting to electromagnetic field.

* * * * *